US00PP37636P2

(12) United States Plant Patent
Heuger

(10) Patent No.: US PP37,636 P2
(45) Date of Patent: Aug. 18, 2026

(54) ***HELLEBORUS* PLANT NAMED 'HL 1062'**

(50) Latin Name: ***Helleborus* x *niger* X *Helleborus* x *hybridus***
Varietal Denomination: HL 1062

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 19/397,971

(22) Filed: Nov. 23, 2025

(51) Int. Cl.
*A01H 5/02* (2018.01)
*A01H 6/72* (2018.01)

(52) U.S. Cl.
USPC ..... Plt./439
CPC ..... *A01H 6/72* (2018.05)

(58) Field of Classification Search
USPC ..... Plt./439
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Helleborus* plant named 'HL 1062', characterized by its upright to outwardly spreading and mounded plant habit; moderately vigorous to vigorous growth habit; dark green-colored leaflets; freely flowering habit; flowers with pinkish white and light purple-colored petals and pinkish white and purplish red-colored sepals; and good garden performance.

2 Drawing Sheets

Figure 1:
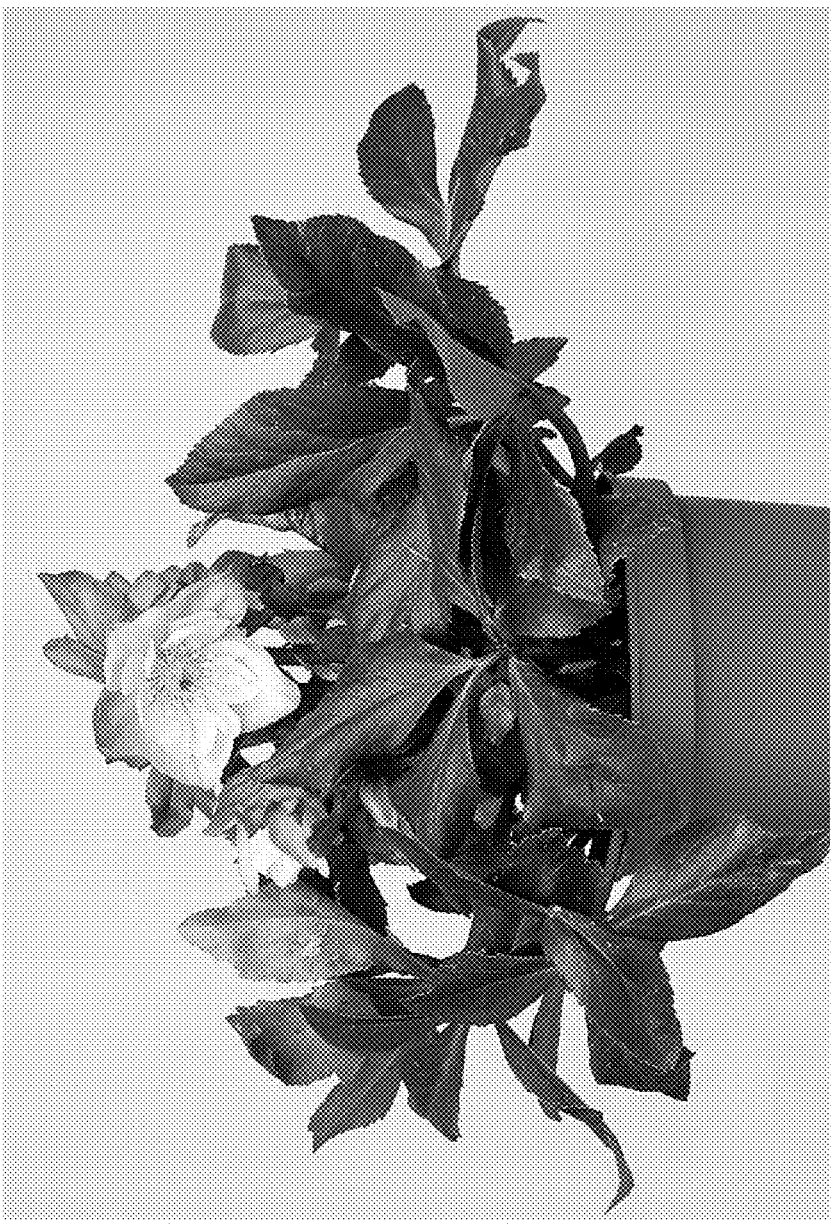

Botanical designation: *Helleborus* x *niger* X *Helleborus* x *hybridus*.

Cultivar denomination: 'HL 1062'.

CROSS-REFERENCED TO CLOSELY-RELATED APPLICATIONS

A European Community Plant Breeder's Rights application for the instant plant was filed by the Inventor/Applicant, Mr. Josef Heuger of Glandorf, Germany, on Nov. 30, 2024, application number 2024/2905. Foreign priority is not claimed to this application.

A United Kingdom Plant Breeder's Rights application for the instant plant was filed by the Inventor/Applicant, Mr. Josef Heuger of Glandorf, Germany, on Aug. 29, 2025, application number 30/988. Foreign priority is not claimed to this application.

BACKGROUND OF THE INVENTION

The present invention relates to a new and distinct cultivar of *Helleborus* plant, botanically known as *Helleborus* x *niger* X *Helleborus* x *hybridus* and hereinafter referred to by the name 'HL 1062'.

The new *Helleborus* plant is a product of a planned breeding program conducted by the Inventor in Glandorf, Germany. The objective of the breeding program was to create new uniform *Helleborus* plants with unique leaf and flower coloration and tolerance to biotic and abiotic stresses.

The new *Helleborus* plant originated from a cross-pollination conducted by the Inventor in Glandorf, Germany in December, 2017 of a proprietary selection of *Helleborus* x *niger* identified as code number 01.0666, not patented, as the female, or seed, parent and a proprietary selection of *Helleborus* x *hybridus* identified as code number 16-08, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in November, 2019.

Asexual reproduction of the new *Helleborus* plant by in vitro axillary meristem culture in a controlled environment in Glandorf, Germany since October, 2020 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HL 1062'. These characteristics in combination distinguish 'HL 1062' as a new and distinct *Helleborus* plant:

1. Upright to outwardly spreading and mounded plant habit.
2. Moderately vigorous to vigorous growth habit.
3. Dark green-colored leaflets.
4. Freely flowering habit.
5. Flowers with pinkish white and light purple-colored petals and pinkish white and purplish red-colored sepals.
6. Good garden performance.

Plants of the new *Helleborus* differ from plants of the female parent selection in the following characteristics:

1. Petals of plants of the new *Helleborus* are not transformed into nectaries whereas petals of plants of the female parent selection are transformed into nectaries.
2. Flower sepals of plants of the new *Helleborus* are pinkish white and purplish red in color whereas flower sepals of plants of the female parent selection are white in color.

Plants of the new *Helleborus* differ from plants of the male parent selection in the following characteristics:

1. Petals of plants of the new *Helleborus* are not transformed into nectaries whereas petals of plants of the male parent selection are partially transformed into nectaries.
2. Flower sepals of plants of the new *Helleborus* are pinkish white and purplish red in color whereas flower sepals of plants of the male parent selection are red in color.

Plants of the new *Helleborus* can also be compared to plants of *Helleborus* x *niger* X *Helleborus* x *hybridus* 'COSEH 5900', disclosed in U.S. Plant Pat. No. 32,340. In side-by-side comparisons, plants of the new *Helleborus* differ primarily from plants of 'COSEH 5900' in the following characteristics:

1. Petals of plants of the new *Helleborus* are not transformed into nectaries whereas petals of plants of 'COSEH 5900' are transformed into nectaries.
2. Flower sepals of plants of the new *Helleborus* are pinkish white and purplish red in color whereas flower sepals of plants of 'COSEH 5900' are white in color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1) is a side perspective view of a typical flowering plant of 'HL 1062' grown in a container.

Figure 2:
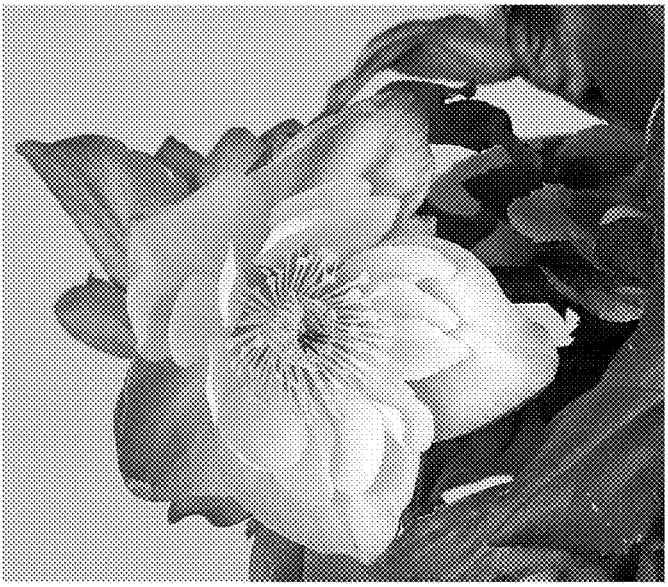

The photograph at the left of the second sheet (FIG. 2) is a close-up view of a typical flower of 'HL 1062'.

Figure 3:
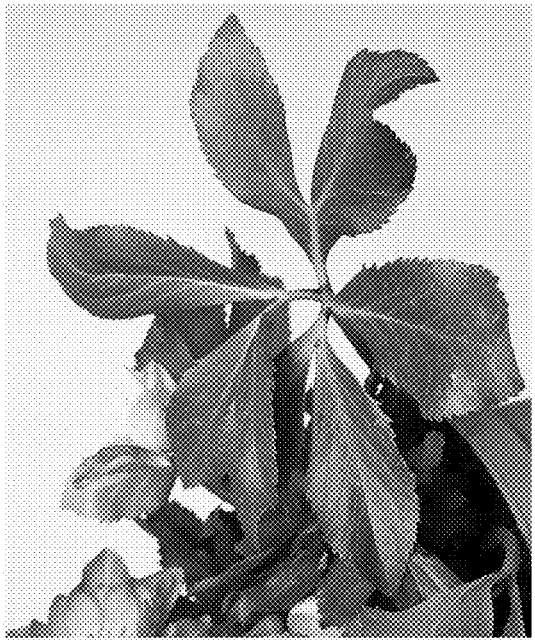

The photograph at the right of the second sheet (FIG. 3) is a close-up view of typical leaflets of 'HL 1062'.

DETAILED BOTANICAL DESCRIPTION

The aforementioned photographs and following observations, measurements and values describe plants grown during the winter in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 5° C. to 12° C. Plants were 48 weeks old when the photographs were taken and 14 months old when the detailed description was taken. In the following description, color references are made to The Royal Horticultural Society Colour Chart, Sixth Edition (2019 reprint), except where general terms of ordinary dictionary significance are used.

Botanical classification: *Helleborus* x *niger* X *Helleborus* x *hybridus* 'HL 1062'.

Parentage:

*Female, or seed, parent*.—Proprietary selection of *Helleborus* x *niger* identified as code number 01.0666, not patented.

*Male, or pollen, parent*.—Proprietary selection of *Helleborus* x *hybridus* identified as code number 16-08, not patented.

Propagation:

*Type*.—In vitro axillary meristem culture.

*Time to initiate roots, winter*.—About 55 days at temperatures about 12° C.

*Time to produce a rooted young plant, winter*.—About 170 days at temperatures ranging from about 4° C. to 15° C.

*Root description*.—Thick to thin, fleshy; typically white to brownish in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright to outwardly spreading and mounding plant habit with flowers held above the foliar plane; plant shape, roughly flattened globular to globular; moderately vigorous to vigorous growth habit and moderate growth rate.

*Plant height, soil level to top of foliar plane*.—About 22.1 cm.

*Plant height, soil level to top of flowers*.—About 24.8 cm.

*Plant diameter* (*area of spread*).—About 41.6 cm.

Leaf description:

*Arrangement*.—Leaves arranged in basal rosettes; leaves palmately compound with typically five leaflets per leaf.

*Leaf length*.—About 19.9 cm.

*Leaf width*.—About 22.9 cm.

*Leaflet length*.—About 12.3 cm.

*Leaflet width*.—About 5.6 cm.

*Leaf shape*.—Palmate; roughly reniform in outline.

*Leaflet shape*.—Ovate to elliptic; slightly convex; about half of the lowest leaflets are cleft.

*Leaflet apex*.—Acute to bluntly acute.

*Leaflet base*.—Attenuate.

*Leaflet margin*.—Serrate; moderately to strongly coarsely undulate.

*Leaflet texture and luster, upper surface*.—Smooth, glabrous; coriaceous and tough; slightly to moderately glossy.

*Leaflet texture and luster, lower surface*.—Smooth, glabrous; coriaceous and tough; slightly glossy.

*Leaflet venation pattern*.—Pinnate and reticulate.

*Leaflet color*.—Developing leaflets, upper surface: Close to 137B; at the base, close to 183B. Developing leaflets, lower surface: Close to 146A; main veins, close to 187B. Fully developed leaflets, upper surface: Close to a blend of NN137A and 147A; at the base, tinged with close to 200A; venation, close to 144A. Fully developed leaflets, lower surface: Close to 147B; venation, close to N144A.

*Petioles*.—Length: About 14.7 cm. Diameter: About 6.5 mm by 7 mm. Strength: Strong. Texture and luster, upper and lower surfaces: Smooth, glabrous; slightly glossy. Color, upper surface: Close to 146D with dots, close to a blend of N186C and 200B. Color, lower surface: Close to 146D; proximally, with dots, close to N186C.

Flower description:

*Flower shape and habit*.—Double rotate bowl-shaped flowers arranged in panicles; freely flowering habit with about three flowers per inflorescence and about 50 flowers and flower buds per plant; flowers face outwardly to slightly nodding.

*Fragrance*.—None detected.

*Natural flowering season*.—Plants begin flowering about ten months after planting; plants flower naturally from early winter into the late winter in Germany.

*Flower longevity on the plant*.—About ten days; sepals persistent, other flower parts are not persistent.

*Flower buds*.—Length: About 2.3 cm. Diameter: About 1.5 cm. Shape: Ovate. Texture and luster: Smooth, glabrous; matte. Color: Upper surface, close to 176B and 176C; lower surface, close to 150D.

*Inflorescence height (including peduncle)*.—About 22.4 cm.

*Inflorescence diameter*.—About 12.9 cm.

*Flower diameter*.—About 9.4 cm.

*Flower depth*.—About 3 cm.

*Petals*.—Quantity and arrangement: About 13 to 15, arranged in a single whorl. Length: About 3.7 cm. Width: About 1.8 cm. Shape: Elliptic. Apex: Bluntly acute. Base: Attenuate. Margin: Entire; not undulate. Texture and luster, upper surface: Smooth, glabrous; matte. Texture and luster, lower surface: Smooth, glabrous; matte to slightly glossy. Color: When opening, upper surface: Close to NN155C; at the base, close to 145C. When opening, lower surface: Close to NN155C; at the base, close to 145C and tinged with close to 182C and 182D. Fully opened, upper surface: Close to N155B; towards the apex and base, tinged with close to 76D; at the base, close to 145B; with subsequent development, color becoming closer to 182B and 182C with the center tinged with close to 151D and at the base, close to 144A and 144B. Fully opened, lower surface: Close to NN155B; flushed with close to 75C; at the base, close to 145C tinged with close to 182C and 182D; with subsequent development, color becoming closer to 183D with the center tinged with close to 151D and at the base, close to 145B tinged with close to 184B.

*Sepals*.—Quantity and arrangement: About five, arranged in a single whorl. Length: About 5.2 cm. Width: About 4.3 cm. Shape: Broadly ovate to broadly elliptic; slightly concave. Apex: Bluntly acute to obtuse. Base: Cuneate. Margin: Entire. Texture and luster, upper surface: Smooth, glabrous; matte. Texture and luster, lower surface: Smooth, glabrous; slightly glossy. Color, upper sepals: When opening, upper surface: Close to NN155C; towards the apex, slightly tinged with close to N155B; at the base, close to 145B. When opening, lower surface: Close to NN155C; towards the apex and base, slightly tinged with close to 75C and 75D; at the base, close to 151D. Fully opened, upper surface: Close to N155B; towards the apex, close to 186A to 186C; at the base, close to 145B. Fully opened, lower surface: Close to NN155C; towards the apex and margins, close to 186B to 186D; at the base, close to 151C. Color, lower sepals: When opening, upper and lower surfaces: Close to NN155C; towards the apex, slightly tinged with close to 151C and 151D; towards the margins, flushed with close to 186B and 186C. Fully opened, upper surface: Close to 186C and 186D; towards the apex and margins, close to 186A to 186C; at the base, close to 145B. Fully opened, lower surface: Close to 185C and 185D; towards the apex, flushed with close to 152B; at the base, close to 152A.

*Flower bracts*.—Quantity per flower: Typically one or two. Length: About 8 cm. Width: About 5.5 cm. Shape: Ovate to elliptic or obovate. Apex: Acute. Base: Truncate to cuneate. Margin: Entire and distally, serrate; coarsely undulate. Color, upper surface: Close to 139A. Color, lower surface: Close to a blend of 146B and 147B; main vein, tinged with close to 187A.

*Peduncles*.—Length: About 14.7 cm. Diameter: About 7 mm to 7.5 mm. Aspect: About 15° from vertical. Strength: Strong. Texture and luster: Smooth, glabrous; moderately glossy. Color: Close to 187B and 187C; heavily covered with fine dots, close to 150C.

*Pedicels*.—Length: About 2.8 cm. Diameter: About 3 mm. Aspect: About 15° from peduncle axis. Strength: Moderately strong. Texture and luster: Smooth, glabrous; moderately glossy. Color: Close to a blend of 181A and 182A; heavily covered with fine dots, close to 150C.

*Reproductive organs*.—Stamens: Quantity per flower: About 100. Filament length: About 1.8 cm. Filament color: Close to 155A. Anther shape: Double and broadly reniform; basifixed. Anther size: About 2 mm by 2.5 mm. Anther color: Close to 154D. Pollen amount: Sparse. Pollen color: Close to 4D. Pistils: Quantity per flower: About six, occasionally, five. Pistil length: About 1 cm. Stigma diameter: About 0.3 mm. Stigma shape: Club-shaped. Stigma color: Close to N155C. Style length: About 0.95 cm. Style color: Close to 183C. Ovary color: Close to 150B and 150C. Seeds and fruits: To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'HL 1062' as herein illustrated and described.

* * * * *